(12) United States Patent
Shao et al.

(10) Patent No.: US 11,887,737 B2
(45) Date of Patent: Jan. 30, 2024

(54) SYSTEM AND METHOD OF MODELING VASCULATURE IN NEAR REAL-TIME

(71) Applicant: ANSYS, INC., Canonsburg, PA (US)

(72) Inventors: Clémentine Shao, Villeurbanne (FR); Michel Rochette, Lyons (FR); Valery Morgenthaler, Villeurbanne (FR)

(73) Assignee: ANSYS, INC., Canonsburg, PA (US)

( * ) Notice: Subject to any disclaimer, the term of this patent is extended or adjusted under 35 U.S.C. 154(b) by 734 days.

(21) Appl. No.: 16/578,140

(22) Filed: Sep. 20, 2019

(65) Prior Publication Data
US 2021/0090743 A1    Mar. 25, 2021

(51) Int. Cl.
| | |
|---|---|
| *G16H 50/50* | (2018.01) |
| *A61B 5/021* | (2006.01) |
| *A61B 5/02* | (2006.01) |
| *A61B 5/00* | (2006.01) |
| *A61B 5/0285* | (2006.01) |
| *G06F 113/08* | (2020.01) |

(52) U.S. Cl.
CPC ............. *G16H 50/50* (2018.01); *A61B 5/021* (2013.01); *A61B 5/02007* (2013.01); *A61B 5/0285* (2013.01); *A61B 5/7278* (2013.01); *A63F 2300/66* (2013.01); *G06F 2113/08* (2020.01)

(58) Field of Classification Search
CPC .... G16H 50/50; A61B 5/02007; A61B 5/021; A61B 5/0285; A61B 5/7278
See application file for complete search history.

(56) References Cited

U.S. PATENT DOCUMENTS

| | | | | |
|---|---|---|---|---|
| 10,297,341 | B2 * | 5/2019 | Itu | G16H 50/50 |
| 2013/0246034 | A1 * | 9/2013 | Sharma | G16H 50/50 |
| | | | | 703/11 |
| 2017/0018081 | A1 * | 1/2017 | Taylor | A61B 6/504 |
| 2017/0329930 | A1 * | 11/2017 | Fonte | A61B 5/7278 |
| 2019/0000325 | A1 * | 1/2019 | Dedroog | A61B 5/021 |

OTHER PUBLICATIONS

"Shuji et al., Lumped parameter model for hemodynamic simulation of congenital heart diseases, Dec. 21, 2017, The Journal of Physiological Sciences", (Year: 2017).*

(Continued)

*Primary Examiner* — Carl H Layno
*Assistant Examiner* — Aya Ziad Bakkar
(74) *Attorney, Agent, or Firm* — Womble Bond Dickinson (US) LLP

(57) ABSTRACT

A system and method of modeling flow of a vasculature in near real-time, is described. A vessel segment of the vasculature is modeled by a reduced order model, and a remainder of the vasculature is modeled by a 0D model. The reduced order model is generated using boundary conditions generated by a 0D model of the entire vasculature. Moreover, the reduced order model of the vessel segment and the 0D model of the remainder of the vasculature can be coupled to simulate flow that can be compared to actual flow measurements to personalize the 0D model of the remainder of the vasculature for a patient. Accordingly, a physician can update parameters of the personalized vascular system model to predict the effects of treatment protocols, including exercise or therapeutic substances, on the patient. Other embodiments are also described and claimed.

24 Claims, 6 Drawing Sheets

(56) References Cited

OTHER PUBLICATIONS

"Yubing Shi et al., Review of Zero-D and 1-D Models of Blood Flow in the Cardiovascular System, Apr. 26, 2011, Biomedical Engineering Online" (Year: 2011).*

"Canel Phillips, A Simple Lumped Parameter Model of the Cardiovascular System, 2011, Colorado State University" (Year: 2011).*

Luca Formaggia, et al., "Numerical Treatment of Defective Boundary Conditions for the Navier-Stokes Equations," [Research Report] RR-4093, Inria, pp. 1-18 (2001).

S. Pant, et al., "A methodological paradigm for patient-specific multi-scale CFD simulations: from clinical measurements to parameter estimates for individual analysis," International Journal for Numerical Methods in BioMedical Engineering, vol. 30, pp. 1614-1648 (2014).

S. Pirola, et al., "On the choice of outlet boundary conditions for patient-specific analysis of aortic flow using computational fluid dynamics," Journal of Biomechanics, vol. 60, pp. 15-21 (2017).

Yubing Shi, et al., "Review of Zero-D and 1-D Models of Blood Flow in the Cardiovascular System," BioMedical Engineering OnLine vol. 10, No. 33, pp. 1-38 (2011).

* cited by examiner

SYSTEM AND METHOD OF MODELING VASCULATURE IN NEAR REAL-TIME

BACKGROUND

Field

The present disclosure relates to systems and methods of modeling cardiovascular systems, and related systems and methods. More specifically, the present disclosure relates to systems and methods of modeling a cardiovascular system of a patient in near real-time.

Background Information

Cardiovascular disease is currently a major cause of death, and a prevalence of the disease continues to increase globally. Cardiovascular disease includes coronary artery disease, stroke, and pathologies of large arteries. For example, coarctation, aneurysm, or aortic dissections of large arteries present a high risk of mortality. Computer models of large arteries have been developed to help understand the physics of the arteries induced by resident pathologies. For example, patient-specific simulations can non-invasively provide clinicians with relevant data like the velocity of the blood, wall pressure, or wall shear stress of large arteries. Such data allows for the diagnosis of disease and supports surgical or treatment options.

Existing models used to describe a compliant artery range in complexity from so-called 0D to 3D models. 0D models, or lumped parameters models, are based on the concept of a hydraulic-electrical analogue. 1D models can describe the wave transport effect since the pressure and flow changes are represented in a full length of the artery studied. When radial changes in the artery need to be detailed, a 2D model can be used. Finally, 3D models are based on computation of the Navier-Stokes equations for a full 3D geometry of the artery. The 3D geometry can be extracted from computed tomography scan or magnetic resonance imaging images to construct a patient-specific model. The patient-specific model can describe local pressure fields, velocity fields, or wall shear stress in the artery, which is necessary to describe complex features such as bifurcations or aneurysms. For this reason, patient-specific 3D model simulations of large arteries can provide useful diagnostic and evaluative information for cardiologists, cardiac surgeons, or other clinicians.

SUMMARY

Although able to provide useful data for clinicians, existing patient-specific 3D model simulations are computationally expensive and impractical to implement in medical protocols. The models, which are typically based on some combination of a 3D computational fluid dynamics model of a vessel segment coupled to a 0D model of a peripheral vasculature, do not provide results in near real-time, e.g., they require hours rather than seconds to conclude. 0D, 1D, 2D or 3D models may refer to deterministic models of physical systems classified dimensionally according to the number of independent space variables of which a system is function of. For example, a 0D model of a system can be based on ordinary differential equations as a function of only one variable (time). A model can also be transient (e.g., time dependent) or steady (e.g., time invariant).

Furthermore, when applied to a large artery segment having several outlets, e.g., an aortic arch of a patient, the existing models usually fail to reach an accurate result. Inaccuracies in the results are caused by numerical instabilities stemming from the selection of unbalanced boundary conditions that do not properly describe the coupling between the large artery segment and the peripheral vasculature. The selection of boundary conditions that are not coherent or physically accurate lead to divergence in the coupled models, which can produce unsatisfactory or even no results. Additionally, since the hemodynamic data used for existing models is generated by medical imaging devices while a patient is obligatorily in a rest state, e.g., lying within a medical scanner, the existing models cannot simulate hemodynamics in another state. More particularly, the clinicians cannot simulate the effect of factors such as exercise or therapeutic substances on the hemodynamics of the patient under evaluation. Thus, the existing models are time-consuming, inaccurate, and have limited value as predictive tools for clinicians.

A system and method of accurately modeling a vasculature of a patient in near real-time is provided. Patient-specific 3D data of a large artery of the vasculature can be obtained, e.g., via medical imaging modalities, and coherent boundary conditions for coupling a 3D model of the large artery to 0D model of the remainder of the vasculature can be determined. The coherent boundary conditions allow a reduced order model of the large artery to be generated, which accurately models the large artery in near real-time. By coupling the reduced order model of the large artery to the 0D model of the remainder of the vasculature, a full model of the cardiovascular system of the patient is built. Furthermore, the full model can provide near real-time simulations. The full model can be optimized based on comparisons to measured flow in the large artery, resulting in a personalized full model of the cardiovascular system. The personalized full model can then be used to evaluate and predict, in near real-time, hemodynamics in the large artery and the remainder of the vasculature for any set of parameters, including parameters that represent the effect of factors such as exercise or therapeutic substances.

In an embodiment, a system models a vascular system of a patient in near real-time. The system receives 3D data representing a vessel segment of a vasculature. The system determines a 0D model of the vessel segment based on static fluid simulations of the vessel segment using the 3D data. The system generates a set of boundary conditions of the vessel segment based on a first vascular system model that includes the 0D model of the vessel segment coupled to a 0D model of a remainder of the vasculature. For example, the set of boundary conditions can include a pressure profile or a flow profile of the vessel segment at the inlet and several outlets, which are coupled to the remainder of the vasculature. The system generates a reduced order model of the vessel segment based on transient fluid simulations of the vessel segment using the set of boundary conditions. For example, the reduced order model of the vessel segment can represent flow in the vessel segment, e.g., can compute pressure at the outlets of the vessel segment, in real-time. Accordingly, the system provides a vascular system model that represents a vascular system in near real-time based on the real-time results of the reduced order model.

In an embodiment, the system personalizes the vascular system model to the patient. The system can receive measured flow data representing measurements of flow in the vessel segment. The system generates simulated flow data representing flow in the vessel segment based on a second vascular system model, which includes the reduced order model of the vessel segment coupled to the 0D model of the remainder of the vasculature. The system adjusts the 0D model of the remainder of the vasculature based on a comparison of the simulated flow data to the measured flow data. Accordingly, the system provides a vascular system model that accurately represents the specific vascular system of the patient in near real-time based on the real-time results of the reduced order model.

In an embodiment, the system predicts the effect of changes in the vascular system model in near real-time. The system receives an input to update parameters of the 0D model of the remainder of the vasculature. For example, the updated parameters can include a change to a resistance, a capacitance, or an inductance of the 0D model of the remainder of the vasculature. The updated parameters can be entered by a physician interested in knowing how the patient will be affected by factors such as exercise or therapeutic substances. The system simulates flow in the vessel segment based on the updated parameters. For example, the updated parameter can be a decreased resistance representative of the lower global blood pressure of the patient induced by a therapeutic substance. The simulated flow can estimate, for example, one or more hemodynamic characteristics of the remainder of the vasculature, or one or more of a flow velocity, a wall shear stress, or a wall pressure of the vessel segment. Accordingly, the system provides a vascular system model that predicts the effect of certain factors on the vascular system of the patient in near real-time.

The above summary does not include an exhaustive list of all aspects of the present invention. It is contemplated that the invention includes all devices, systems, and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
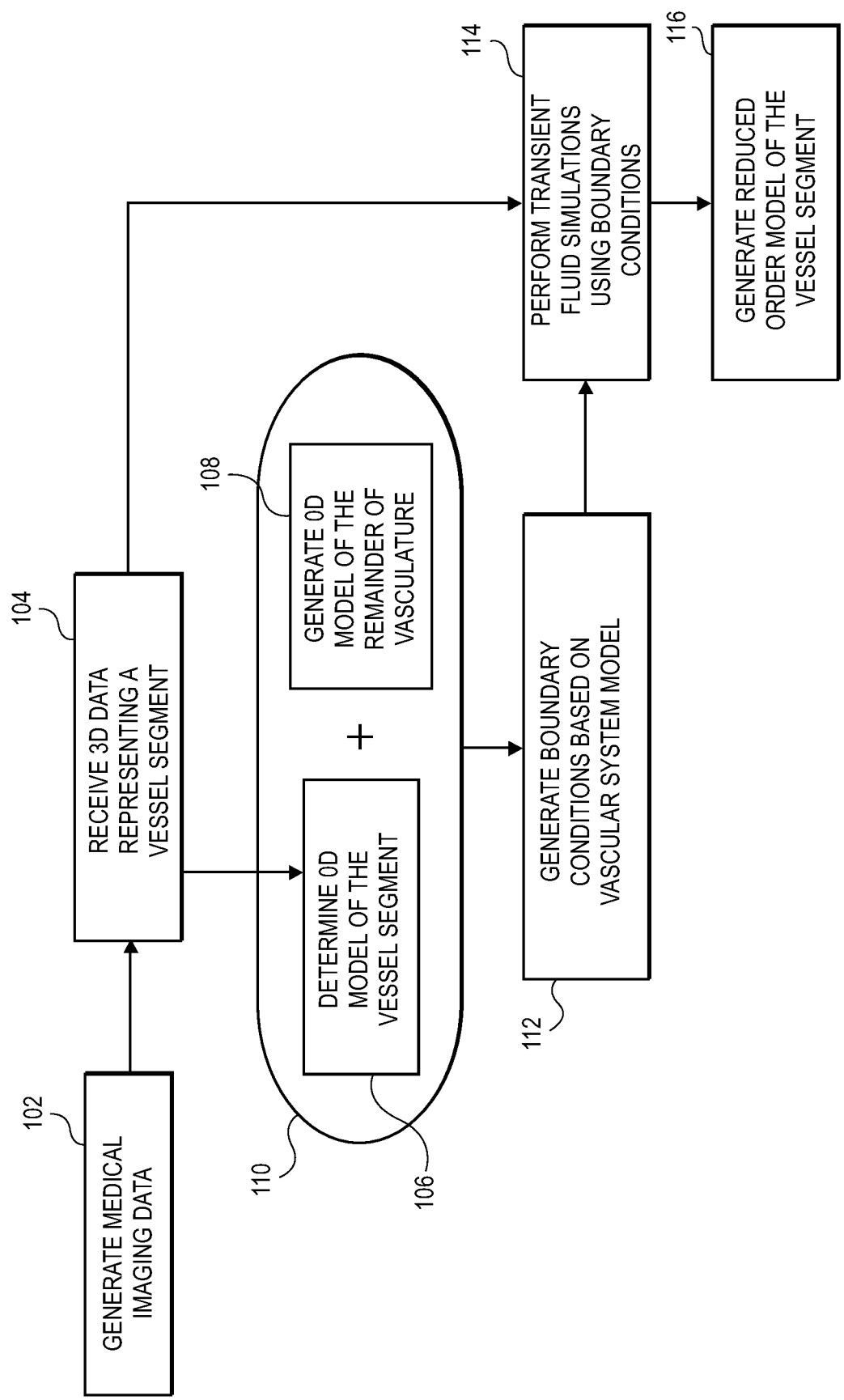
FIG. 1 is a flowchart of a method of generating a reduced order model of a vessel segment, in accordance with an embodiment.

Embodiments describe a system and method of modeling hemodynamics of a vasculature in near real-time. The vasculature can include a vessel segment, e.g., a large artery, and a remainder of the vasculature, e.g., a vascular network connected to the vessel segment. A vascular model can include a reduced order model of the vessel segment, which represents flow in the vessel segment in real-time, coupled to a 0D model of the remainder of the vasculature. The system and method can be embodied as software running on a medical imaging system or a standalone computer.

In various embodiments, description is made with reference to the figures. However, certain embodiments may be practiced without one or more of these specific details, or in combination with other known methods and configurations. In the following description, numerous specific details are set forth, such as specific configurations, dimensions, and processes, in order to provide a thorough understanding of the embodiments. In other instances, well-known processes and manufacturing techniques have not been described in particular detail in order to not unnecessarily obscure the description. Reference throughout this specification to "one embodiment," "an embodiment," or the like, means that a particular feature, structure, configuration, or characteristic described is included in at least one embodiment. Thus, the appearance of the phrase "one embodiment," "an embodiment," or the like, in various places throughout this specification are not necessarily referring to the same embodiment. Furthermore, the particular features, structures, configurations, or characteristics may be combined in any suitable manner in one or more embodiments.

The use of relative terms throughout the description may denote a relative position or direction. For example, "distal" may indicate a first position along a flow path within a vessel segment. Similarly, "proximal" may indicate a second position in an opposite direction, e.g., upstream, from the first direction along the flow path. Such terms are provided to establish relative frames of reference, however, and are not intended to limit the systems or methods to a specific configuration described in the various embodiments below.

In an aspect, an accurate and near real-time model of a cardiovascular system is modeled using dynamic reduced order modeling, in part, rather than 3D transient fluid simulation. The model of the cardiovascular system includes a reduced order model of a vessel segment coupled to a 0D model of a remainder of the vasculature. Coupling between the model portions is stable because the reduced order model derives from 3D transient fluid simulations having coherent boundary conditions, as described in detail below. The model simulates the cardiovascular system in near real-time, e.g., within seconds, which allows the 0D model of the remainder of the vasculature to be personalized to a particular patient through optimization. After the model is calibrated for the patient, hemodynamic data like the wall pressure, flow velocity, and wall shear stress fields of the considered geometry can be accessed in near real-time for any set of parameters of the patient (including parameters representative of the patient impacted by factors such as a therapeutic substance or exercise.

Referring to FIG. 1, a flowchart of a method of generating a reduced order model of a vessel segment is shown in accordance with an embodiment. The reduced order model can be a patient-specific reduced order model of the vessel segment, e.g., an aortic cross of a particular patient. As described below, the reduced order model can be based on the results of several 3D transient fluid simulations using different sets of coherent boundary conditions. Furthermore, the dynamic, e.g., time-dependent, reduced order model can return 3D results describing hemodynamics in the vessel segment for any set of boundary conditions.

At operation 102, medical imaging data can be generated by a medical imaging system. For example, the medical imaging can include a medical scanner, such as a computed tomography (CT) scanner or a magnetic resonance imaging (MRI) scanner. The medical scanner may also be medical ultrasound equipment. The medical scanner can capture one or more of geometric and/or flow data of the vascular system of a patient. For example, the CT scanner can provide geometric data of the vascular system, and the MRI scanner can provide geometric and flow data of the vascular system. A phase contrast MRI scanner can capture MRI 2D data or MRI 4D data of a vessel segment. MRI 2D data represents a geometric envelope of the vessel segment and describe flow as a function of time, e.g., mass flow rate, at a cross-section of the geometric envelope. MRI 4D data represents the geometric envelope of the vessel segment and describes flow at any point within the geometric envelope at any time during the scan. Similar data can be generated by a CT scanner to represent the vascular system or any portion thereof, e.g., the vessel segment.

The MRI scan, CT scan, or echocardiogram data obtained for the vascular system of a particular patient allows a physician to measure the hemodynamics within the vessels when the patient is at rest. Such data does not, however, represent how the blood flow interacts with the vasculature, e.g., a wall pressure or a wall stress of the vessels caused by the blood flow. Nor does the scan data inform the physician about how the hemodynamics are likely to change under other conditions, e.g., when the patient is not at rest. Accordingly, the medical scan data does not meet the need to understand whether the vascular system is currently diseased or at risk of disease.

Transient fluid simulations can be performed using the medical scan data. It will be understood, however, that it is impractical to extract the 3D geometry of a full cardiovascular system using the medical imaging techniques that provide the 3D geometry and flow data. Furthermore, resolving a 3D simulation of the complete network using the geometry and flow data for the full cardiovascular system would be highly time consuming. For this reason, only a truncated part of the vessels are simulated to determine flow, wall pressure, or wall shear stress of the vascular segment of interest.

Figure 2:
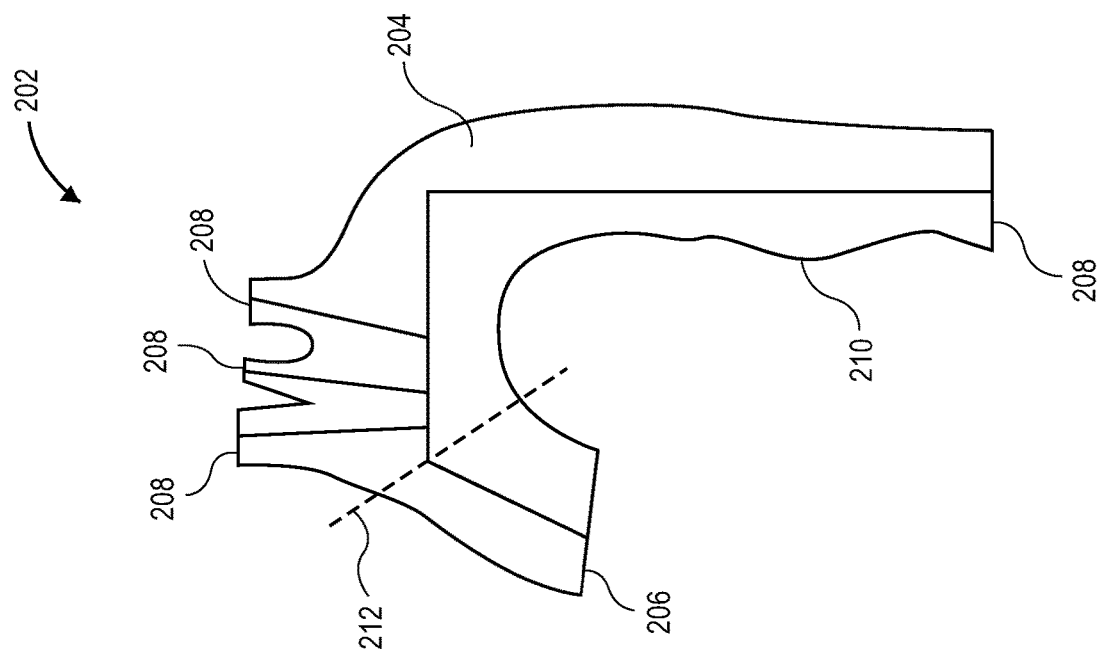
FIG. 2 is a graphical view of 3D data representing a vessel segment, in accordance with an embodiment.

Referring to FIG. 2, a graphical view of 3D data representing a vessel segment is shown in accordance with an embodiment. At operation 104 (FIG. 1), 3D data 202 representing a vessel segment 204 of the vascular system is received. The 3D data 202 can represent a geometry and/or flow of the vessel segment 204. By way of example, the vessel segment 204 can be an aortic arch of the vascular system of the patient. The aortic arch can include an inlet 206 and several outlets 208. In the case of the aortic arch, the inlet 206 can correspond to an end of the ascending aorta, and the outlets 208 can include the brachiocephalic, the left subclavian, the left carotid, and the beginning of the descending aorta. The 3D data 202 can include geometric data representing the inlet 206, the outlets 208, and a vessel wall 210 defining an envelope of the vessel segment 204.

In an embodiment, the 3D data from the medical scanner can be manually or automatically segmented to obtain 3D geometric data of the vessel segment 204. The extracted data set can include 246 slices of 512×512 pixels. Each slice can have a thickness of 1.25 mm, and each pixel can have a pixel size of 0.81 mm. The obtained geometry can be smoothed, and the outlets 208 may be cropped to be plane surface. The obtained surface can then be meshed with 8 prism layers on the vessel wall 210 and polyhedral elements to represent the vessel segment 204, as shown in FIG. 2. The flow at each outlet 208 of the vessel segment 204 can also be registered from the 3D data 202. More particularly, flow measurements can be extracted for each outlet 208 over a period of one cardiac cycle. Accordingly, the 3D data 202 representing the vessel segment 204 can provide both the geometry data and the flow data for the vascular segment of interest.

Although transient fluid simulations of the vessel segment 204 could be performed using the extracted 3D data, such simulations require approximation of the boundary conditions at the inlet 206 and the outlets 208 of the vessel segment 204. Studies have shown that different formulations of the boundary condition at the inlet 206 and outlets 208 can quantitatively change the results of flow rate, flow velocity, or the wall shear stress in the simulated vessel segment 204. Thus, the boundary conditions that are used in the 3D transient fluid simulations are critical to effectively modeling the vasculature.

Existing techniques of determining boundary conditions for simulating the truncated vessel segment fail to accurately represent the coupling between the truncated vessel segment 204 and the vascular network. More particularly, the existing techniques are ineffective in the case of vessel segments 204 having several outlets 208 because the models do not correlate the outlets 208, which can lead to numerical instabilities in the simulation. Accordingly, it is discovered that to accurately and stably model the vessel segment 204 in 3D, an initial boundary condition solution must be provided to properly represent the coupling between the truncated vessel segment 204 and the peripheral vasculature.

To develop a coherent set of boundary conditions of the vessel segment 204 for 3D transient fluid simulation, after the geometry of the considered part of the vasculature is extracted from the medical scan data, the vessel segment 204 is first represented with a 0D model. In a 0D model, blood flow rate is equivalent to electrical current and blood pressure drop between two points is equivalent to voltage. A segment of an artery can be modeled with a capacitor (to model the effect of vascular compliance due to elasticity of the vessel wall 210), a resistor (to model the effect of frictional loss), and an inductor (to model the blood inertia).

The equivalent 0D model of the vessel segment 204 is based on a segmentation of the 3D geometry. More particularly, the 3D geometry can be divided into several segments. For example, in FIG. 2, the segments can include a first segment extending from the inlet 206 to a proximal plane 212, and several other segments extending between the proximal plane 212 and the outlets 208 at the brachiocephalic, the left subclavian, the left carotid, and the beginning and the descending aorta.

Figure 3:
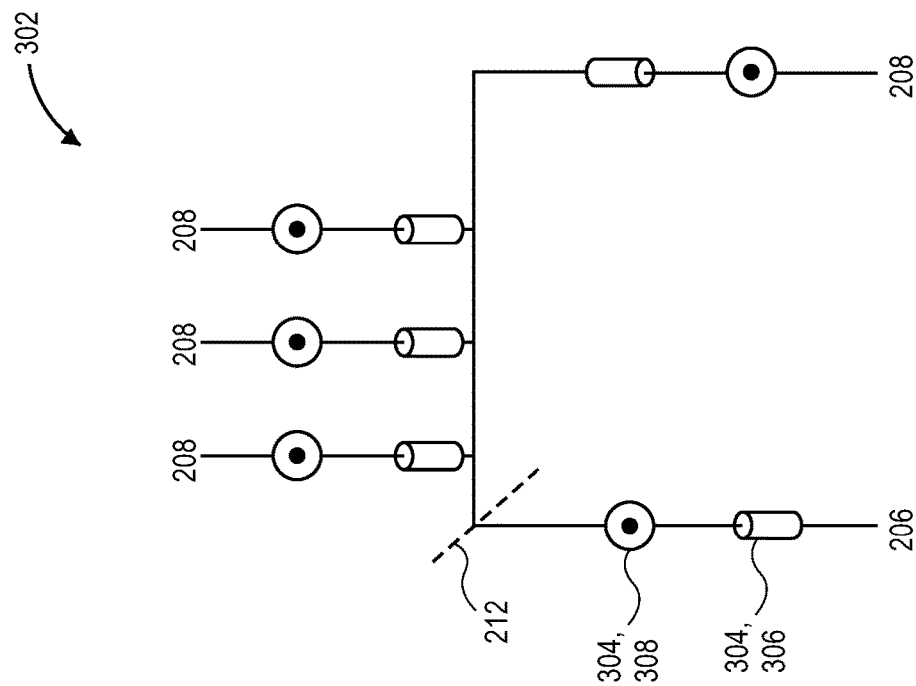
FIG. 3 is a graphical view of a 0D model of a vessel segment, in accordance with an embodiment.

Referring to FIG. 3, a graphical view of a 0D model of a vessel segment is shown in accordance with an embodiment. At operation 106 (FIG. 1), a 0D model 302 of the vessel segment 204 is determined. The 0D model can include one or more 0D elements 304. Each 0D element 304 can be an element of a particular type, e.g., capacitors, resistors, or inductors, for each segment of the divided 3D geometry. By way of example, the first segment between the inlet 206 and the proximal plane 212 can include an inductor 306 in series with a pressure source 308 to represent the segment in a hydraulic-electrical analogue.

The 0D model 302 of the vessel segment 204 can be based on static fluid simulations of the vessel segment 204 using the 3D data 202. More particularly, to obtain parameters for the 0D elements 304 of the 0D model 302, static fluid simulations of the 3D geometry can be run to create a response surface that accurately represents the hydrodynamic behavior of the vessel segment 204. The response surface can return the pressure drop in each segment as a function of the pressure at the inlet 206 and the flow at the outlets 208. Variations in the mass flow rate at the outlets 208 is known over a cardiac cycle based on the 3D data 202 taken from the medical scans. Furthermore, the range of variation in pressure at the inlet 206 is known from the literature. For example, the range of pressure variation can be found in W. B. Kannel, "Historic perspectives on the relative contributions of diastolic and systolic blood pressure elevation to cardiovascular risk profile," *Am. Heart J.*, Vol. 138, No. 3, Supplement, pp. S205-S210, September 1999. Such information can be used to determine the pressure at the inlet 206 and the mass flow rate at the outlets 208 over the period between systole and diastole. For example, the pressure at the inlet 206 can be determined to vary between 10,000 and 20,000 Pascal and the flow at the outlets 208 can vary between −0.1 and 0.7 kg/s during the cardiac cycle. Some of the generated data may not be physically possible (for instance when the data represents a high value of flow that is fixed at the smallest outlet 208 and small or negative flow values at the rest of the outlets 208). The response surface can be computed using the genetic aggregation algorithm. Validations points can be simulated to evaluate the quality of the generated response surface. A maximum absolute error can be less than 3%. To represent the transient effects, an inductance may be added in each segment. The value of the inductance can be calculated using the geometric assumption that each segment is a perfect cylinder and based on the law of Poiseuille with the following formula: $L=(9*\rho*\Delta l)/(4*\pi*r^2)$, where l is a length of the cylinder, r is a radius of the cylinder, and $\rho$ is the blood density. Accordingly, each segment of the vessel segment 204 can be represented using a respective inductor 306 and a respective pressure source 308. The values for the inductors 306 are calculated from the law of Poiseuille and the values for the pressure sources 308 are taken from the response surface of the static simulations to accurately represent the pressure and flow interaction of the vessel segment 204.

Figure 4:
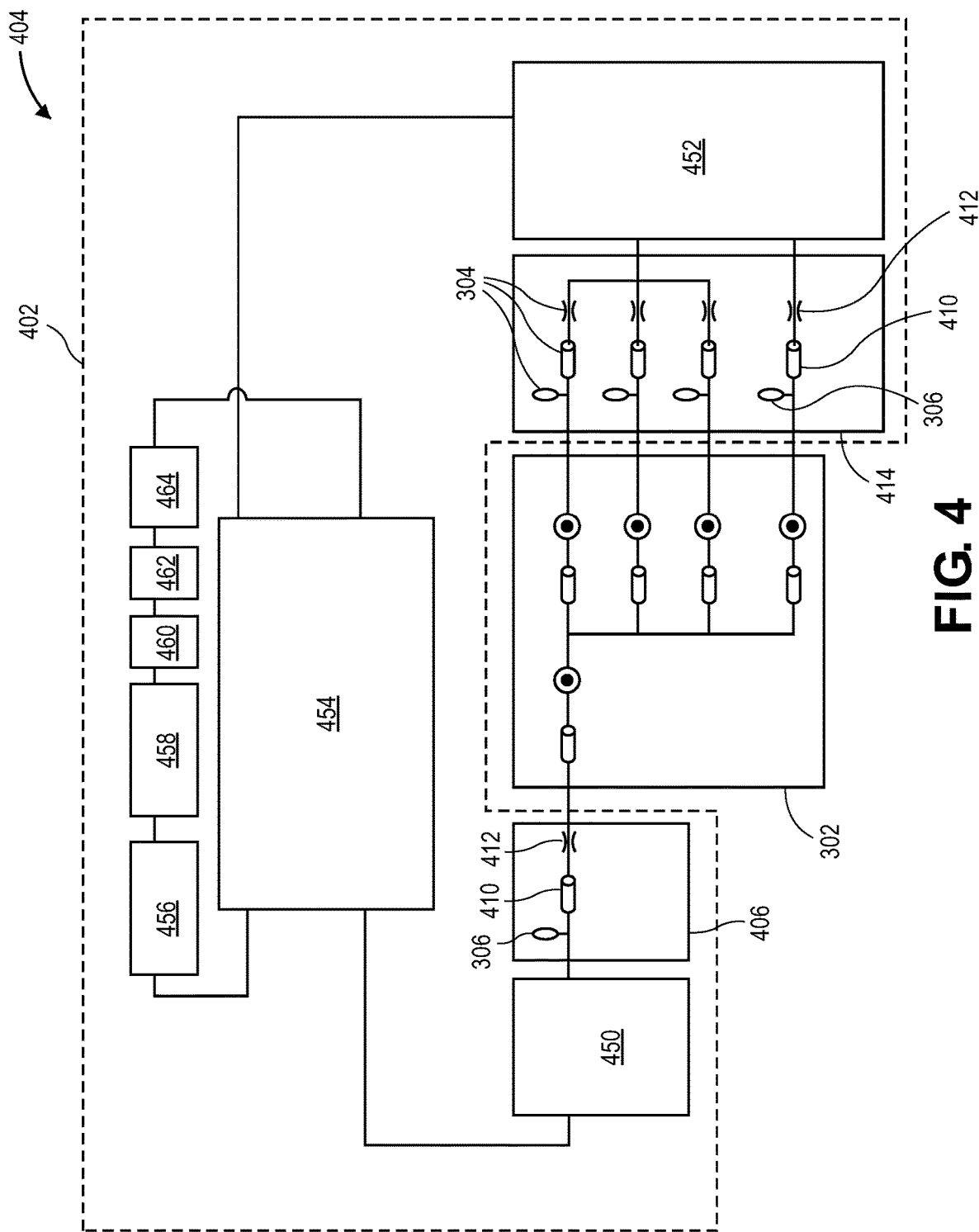
FIG. 4 is a graphical view of a first vascular system model including a 0D model of a vessel segment coupled to a 0D model of a remainder of a vasculature, in accordance with an embodiment.

Referring to FIG. 4, a graphical view of a first vascular system model including a 0D model of a vessel segment coupled to a 0D model of a remainder of a vasculature is shown in accordance with an embodiment. At operation 108 (FIG. 1), a 0D model 402 of the remainder of the vasculature can be generated. The 0D model 402 of the remainder of the vasculature can include several model blocks representing different portions of the peripheral vasculature. For example, an ascending aorta block 406 representing the ascending aorta between the heart and the inlet 206 of the vessel segment 204 may include 0D elements 304, such as an inductor 306, a capacitor 410, and a resistor 412 in series. The model block represents the peripheral ascending aorta that is not captured in the 3D data 202. Similarly, a systemic artery block 414 representing the arteries connected to the outlets 208 of the vessel segment 204 may include 0D elements 304, such as inductors 306, capacitors 410, and resistors 412. The model block represents the peripheral arteries that are not captured in the 3D data 202. Additional model blocks representing respective portions of the vascular system can be provided. A model block 450 can represent a systemic aortic sinus, a model block 452 can represent arterioles, capillaries, and veins, a model block 454 can represent the heart, a model block 456 can represent a pulmonary artery sinus, a model block 458 can represent a pulmonary artery, a model block 460 can represent pulmonary arterioles, a model block 462 can represent pulmonary capillaries, and a model block 464 can represent pulmonary veins. The model blocks representing the remainder of the vasculature can include model element 304 representing hemodynamics of the anatomical features, which are not captured in the 3D data 202. The model blocks can be interconnected to provide the 0D model 402 of the remainder of the vasculature. The parameters, e.g., the resistances, the inductances, or the capacitances, of the model elements in each of the model blocks of the 0D model 402 of the remainder of the vasculature can be set using values taken from the literature.

As a next operation toward generating the coherent set of boundary conditions, at operation 110 (FIG. 1), a first vascular system model 404 can be generated by combining the 0D model 302 of the vessel segment 204 with the 0D model 402 of the remainder of the vasculature, e.g., the vascular network connected to the vessel segment 204. The 0D model 402 of the remainder of the vasculature can be coupled to the vessel segment 204 as shown in FIG. 4 to create the first vascular system model 404.

Referring again to FIG. 1, at operation 112, a set of boundary conditions of the vessel segment 204 is generated based on the first vascular system model 404. The first vascular system model 404 having the 0D model of the full cardiovascular system (the 0D model 302 of the vessel segment 204 coupled to the 0D model 402 of the remainder of the vasculature) can be used to extract coherent boundary conditions. Coherent boundary conditions refer to boundary conditions that correlate the outlets 208 of the vessel segment 204. The first vascular system model 404 can run over one or more cardiac cycles until the model stabilizes. More particularly, the model can run until flow and pressure curves generated by the model are identical from one cardiac cycle to a next cardiac cycle. Initially, flow will be distributed mainly in the capacitor elements of the model, however, after several cardiac cycles the flow will be distributed throughout the model elements and the flow and pressure curves will stabilize. When the model is stabilized, several seconds of flow and pressure data can be recorded. For example, pressure at the outlets 208 and flow at the inlet 206 of the vessel segment 204 can be recorded for a first set of parameters of the full cardiovascular model. Accordingly, the set of boundary conditions can include one or more of a pressure profile or a flow profile of the vessel segment 204 for a respective set of model parameters.

The parameters of the full cardiovascular model, e.g., resistances, capacitances, inductances, and elastances of the model blocks, may be changed to create additional sets of boundary conditions corresponding to the changed parameters. More particularly, the parameters can be varied over a range of values, and each variation can generate a corresponding set of boundary conditions, e.g., pressure or flow profiles of the vessel segment 204 for the patient having the changed parameters. The various sets of boundary conditions may be representative of changes in the patient, such as changes in heart rate, blood pressure, etc. For example, the variations in parameters can correspond to a variation in heart rate between 50 to 120 beats per minute, or a blood pressure range of 19,000 to 3000 Pascal. Accordingly, the parameters of the first vascular system model 404 are varied to produce pressure and flow curves for the vessel segment 204 that includes a high range of variation covering the different scenarios.

At operation 114, transient fluid simulations for the vessel segment 204 are carried out using the boundary conditions generated at operation 112. It is notable that the boundary conditions generated by the 0D model of the full cardiovascular system are coherent. The transient fluid simulations based on the coherent boundary conditions are likely to converge on a satisfactory solution.

The transient fluid simulations can be performed on the 3D geometry from the 3D data 202 received at operation 104. For example, the 3D geometry can include the vessel segment 204 meshed with polyhedral elements and prism layers on the vessel wall 210. The mesh of the 3D geometry of the vessel segment 204 may be composed of polyhedral elements and 8 prisms layers on the vessel wall 210. The final mesh can have 193,037 cells and 534,160 nodes. The blood can be modeled as an incompressible Newtonian fluid with constant density (rho=1056 kg/m$^3$) and viscosity (mu=0.0035 Pa*s). Turbulence can be modeled with a scale adaptive simulation model.

The transient fluid simulations can include a mass flow profile applied at the inlet 206 of the vessel segment 204 and pressure profiles applied at the outlets 208 of the vessel segment 204. The flow and pressure profiles can be the boundary conditions resulting from operation 112. The transient fluid simulations can simulate transient fluid characteristics over several seconds, e.g., 3 seconds, using a constant time step of 0.001 seconds to simulate approximately 3 cardiac cycles. The average pressure and flow at the inlet 206 and outlets 208 can be saved at each time step, and one or more of the pressure field, the velocity field, or the wall shear stress at the vessel wall 210 can be saved every ten-time steps.

Numerous transient fluid simulations can be performed to generate simulation results, each simulation performed using a respective one of the set of boundary conditions generated by the 0D model of the full cardiovascular system. For example, 15 sets of boundary conditions may have been generated, and 15 corresponding transient fluid simulations can be run. The corresponding transient fluid simulations can compute numerous sets of results for wall shear stress, wall pressure, and blood velocity profiles that can be used to compute a dynamic reduced order model of the vessel segment 204.

At operation 116, a reduced order model of the vessel segment 204 is generated based on the transient fluid simulations of the vessel segment 204 from operation 114. Reduced order modeling is relatively well mastered for most dynamic linear systems. The ANSYS LTI-ROM (Linear Time Invariant Reduced Order Model) is representative of the state of the art in this field. Examples of such systems and methods for building nonlinear dynamic reduced order models from any physical solver solution are described in U.S. Provisional Patent Application No. 62/773,555, filed on Nov. 30, 2018, and entitled "Systems and Methods for Building Dynamic Reduced Order Physical Models," the contents of which are incorporated herein by reference.

The transient fluid simulations provide the physical solver solution upon which the reduced order model of the vessel segment 204 is based. The results of the transient fluid simulations, which were based on coherent boundary conditions, can be divided into learning and validation cases to compute different reduced order models of the vessel segment 204. The reduced order models correspond to an identification of the nonlinear differential equations that relate solver inputs to solver outputs. For example, the input of the different reduced order models can be the boundary conditions used for the simulations, and the reduced order models can learn different results as a function of the boundary conditions. Accordingly, a reduced order model can return 3D results based on the boundary conditions. For example, separate reduced order models can be generated to return blood flow at the outlets 208 of the vessel segment 204, blood pressure at the vessel wall 210, wall shear stress at the vessel wall 210, pressure fields of the blood pressure at the vessel segment 204, and velocity fields of the blood flow in the vessel segment 204. The reduced order models can be computed from learning cases and validation cases divided from the transient fluid simulations. Accordingly, for any boundary condition inputs, e.g., boundary conditions applied by the 0D model 402 of the remainder of the vasculature, the reduced order models can compute a corresponding 3D output of the vessel segment 204 in real-time.

A reduced order model can be generated to replace the equivalent model of the vessel segment 204 in the vascular system model. One of the reduced order models developed at operation 116 can compute average blood flow at the outlets 208 of the vessel segment 204. In a system simulation, the 0D model 402 of the remainder of the vasculature may be more stable, however, when it is coupled with a module simulating the vessel segment 204 that returns the pressure drop in the vessel segment 204 as a function of the flow in the vessel segment 204. This is actually the opposite of the reduced order model that computes average blood flow at the outlets 208 of the vessel segment 204. The pressure/flow functions at the outlets 208 and the inlet 206 of the vessel segment 204 is bijective, however, and can be reversed. Accordingly, a reduced order model that takes as an input the flow at each outlet 208 and a pressure at the inlet 206 to return the pressure at the outlets 208 can be developed. In an embodiment, this derivative reduced order model of the vessel segment 204 can be used to replace the equivalent model of the vessel segment 204 in the vascular system model.

Figure 5:
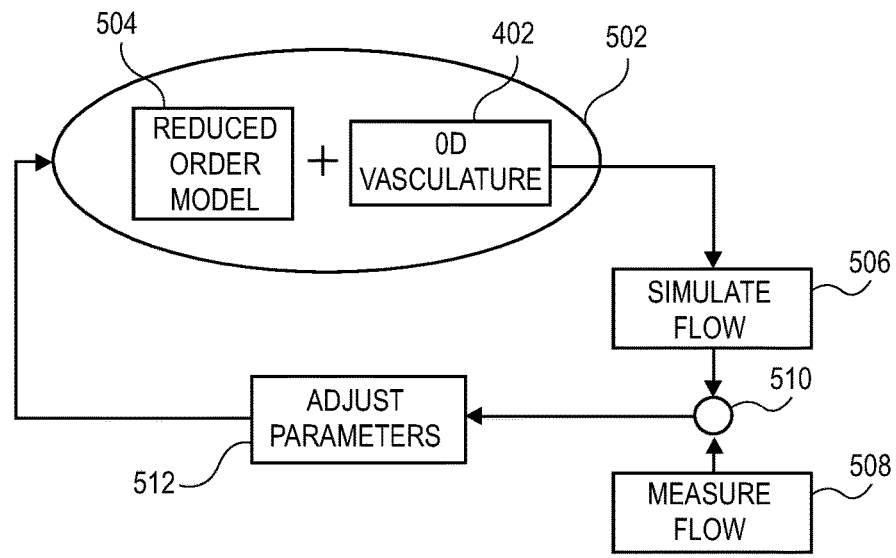
FIG. 5 is a flowchart of a method of calibrating a 0D model of a remainder of a vasculature based on a comparison of simulated flow data and measured flow data, in accordance with an embodiment.

Referring to FIG. 5, a flowchart of a method of calibrating a 0D model of a remainder of a vasculature based on a comparison of simulated flow data and measured flow data is shown in accordance with an embodiment. When the derivative reduced order model 504 of the vessel segment 204 is built, it can be combined with the 0D model 402 of the remainder of the vasculature to simulate hemodynamics in the full cardiovascular system. More particularly, at operation 502, a second vascular system model (FIG. 6) can be formulated to include a reduced order model 504 of the vessel segment 204 coupled to the 0D model 402 of the remainder of the vasculature.

Figure 6:
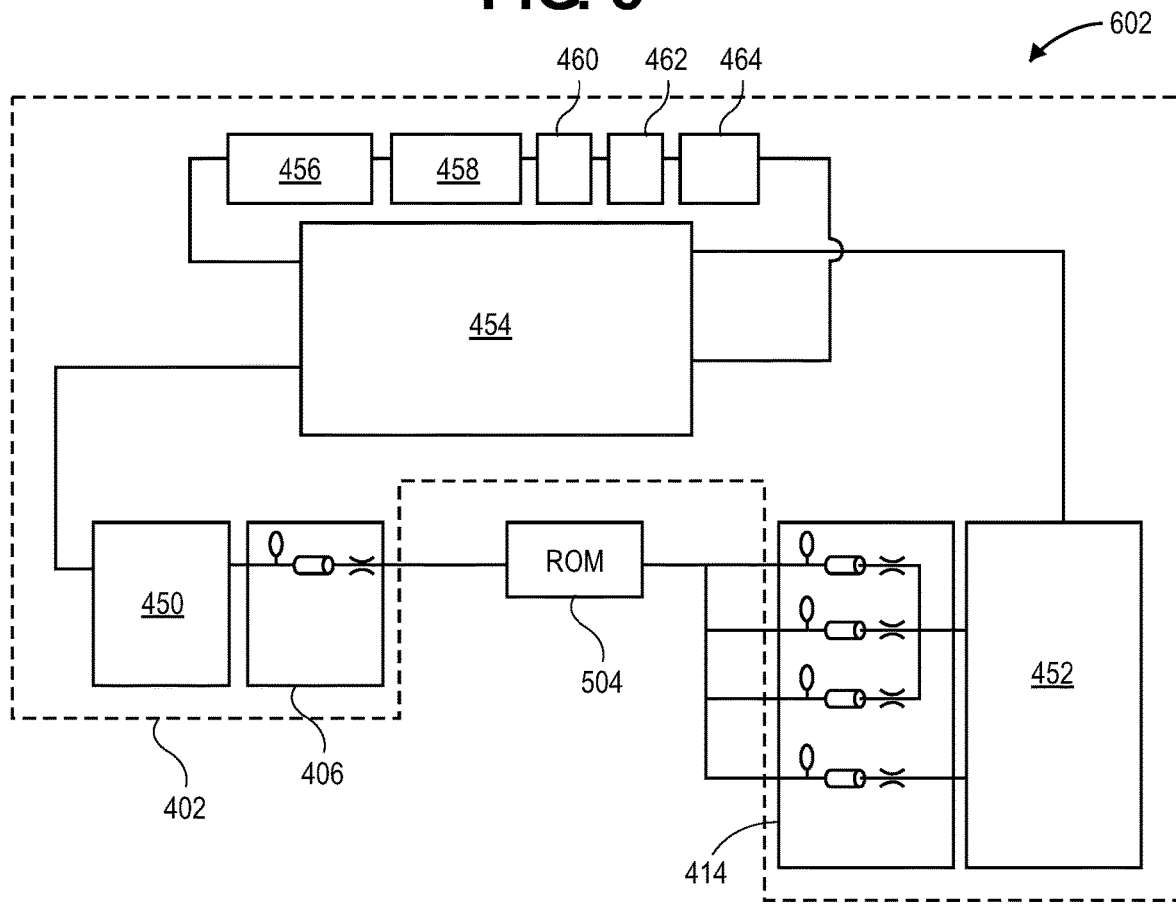
FIG. 6 is a graphical view of a second vascular system model including a reduced order model of a vessel segment coupled to a 0D model of a remainder of a vasculature, in accordance with an embodiment.

Referring to FIG. 6, a graphical view of a second vascular system model including a reduced order model of a vessel segment coupled to a 0D model of a remainder of a vasculature is shown in accordance with an embodiment. A second vascular system model 602 can be similar to the first vascular system model 404, however, the first equivalent model of the vessel segment 204 in the first vascular system model 404 is replaced by the reduced order model 504 of the vessel segment 204 in the second vascular system model 602. The reduced order model 504 can take as input the pressure at the inlet 206 of the vessel segment 204 and flow at the outlets 208 of the vessel segment 204, and return the pressure at the outlets 208. Accordingly, the reduced order model 504 of the vessel segment 204 can be coupled to the 0D model 402 of the remainder of the vasculature to provide the inlet 206 and outlet 208 conditions of the vessel segment 204 as inputs to the 0D model 402 of the remainder of the vasculature. The second vascular system model 602, which is based on the accurate and patient-specific model of the vessel segment 204, can be optimized in order to further refine and personalize the 0D model 402 of the remainder of the vasculature for the patient.

Referring again to FIG. 5, at operation 506 simulated flow data is generated representing flow in the vessel segment 204. The simulated flow data is based on the second vascular system model 602. It will be understood that the reduced order model 504 of the second vascular system model 602 replaces the 0D model 302 of the vessel segment 204 in the first vascular system model 404. The simulated flow data generated by the second vascular system model 602 is therefore more accurate than the first vascular system model 404 results, because the reduced order model 504 is based on transient simulations instead of static simulations.

At operation 508, measured flow data representing measurements of flow in the vessel segment 204 are received. The measurements of flow can be taken in real-time from the patient by medical imaging equipment. For example, the medical scanner can generate CT or MRI scan data for the vessel segment 204 to quantify the blood flow.

At operation 510, the simulated flow data generated at operation 506 can be compared to the measured flow data generated at operation 508. The comparison can be used to calibrate the second vascular system model 602. More particularly, the 0D model 402 of the remainder of the vasculature can be dynamically customized to make the simulated data fit the measured data. At operation 512, a function to minimize the difference between the measured and simulated flow can be used to adjust the 0D model 402 of the remainder of the vasculature. For example, the Levenberg-Macquardt algorithm can be used to calibrate the parameters, e.g., resistance, capacitance, or inductance, of the 0D model elements in the model blocks. The calibrated parameters can also include the elastance parameters of the heart model block. The function to minimize is the mean square error obtained from the difference of the flow in the different outlets 208 from the measured flow data at operation 508 and the simulated flow data at operation 506. The parameters of the 0D model 402 of the remainder of the vasculature can be adjusted based on the comparison.

The simulated flow and measured flow can be generated and compared over several iterations until the parameters of the 0D model 402 of the remainder of the vasculature are adjusted such that the simulated flow data fits the measured flow data. When the simulated and measured flow match, the second vascular system model 602 is personalized to the patient. It will be appreciated that this personalization can be performed rather quickly, even when many iterations are performed. More particularly, the reduced order model 504 can be computed in real-time, allowing the second vascular system model 602 to simulate the cardiac cycle in near real-time. For example, the second vascular system model 602 can simulate ten seconds of the cardiac cycle in less than a minute, e.g., within 20-30 seconds. At this simulation rate, personalization can be achieved within minutes or hours. Accordingly, personalization of the cardiovascular system model can be incorporated in a medical protocol for performing a medical scan of a patient. By contrast, personalization of a cardiovascular system model without the reduced order model 504 of the vessel segment 204 could take very long, e.g., days, to perform, and would not be practical to incorporate in the clinical setting.

Figure 7:
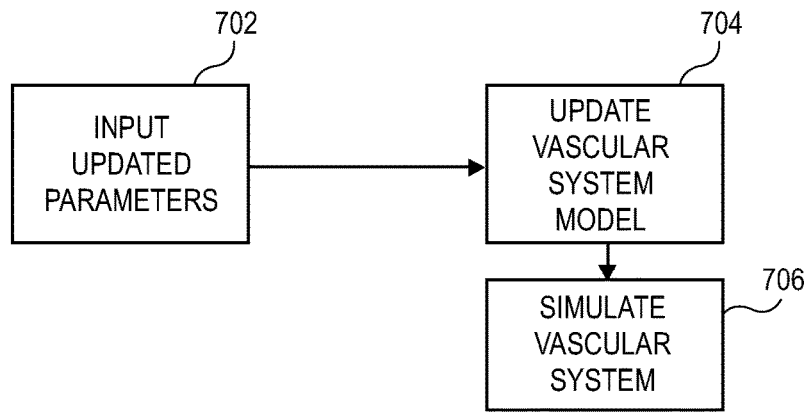
FIG. 7 is a flowchart of a method of interactively evaluating hemodynamic characteristics of a vascular system based on updating parameters of a personalized model of the vascular system, in accordance with an embodiment.

Referring to FIG. 7, a flowchart of a method of interactively evaluating hemodynamic characteristics of a vascular system based on updating parameters of a personalized model of the vascular system is shown in accordance with an embodiment. When the personalized model of the cardiovascular system is obtained, a physician can use the optimized model to generate 3D simulation results dynamically in response to an update of parameters of the 0D model 402 of the remainder of the vasculature.

At operation 702, an input from the physician can be received by the system to update parameters of the 0D model 402 of the remainder of the vasculature. The updated parameters can be one or more of resistances, capacitances, inductances, or elastances of 0D model elements of the model blocks. More particularly, the physician can input parameter changes that correspond to certain factors, such as exercise, the use of therapeutic substances by the patient, or other real-life situations that affect the model parameters. Accordingly, the input can be a request to adapt the model to allow for the evaluation or the prediction of the respective factor on the patient.

At operation 704, the second vascular system model can be updated with the parameter changes input by the physician. For example, one or more of resistances, capacitances, inductances, or elastances of the 0D model 402 of the remainder of the vasculature, which is coupled to the reduced order model 504 of the vessel segment 204, can be updated. At operation 706, flow in the vascular system, including flow in the vessel segment 204, can be simulated in near real-time using the updated second vascular system model 602.

The simulated flow can result in estimates of 3D results of the vessel segment 204 or the remainder of the vasculature in near real-time. For example, the simulated flow can estimate one or more hemodynamic characteristics of the remainder of the vasculature. Such hemodynamic characteristics can include a systemic blood pressure, for example.

Figure 8:
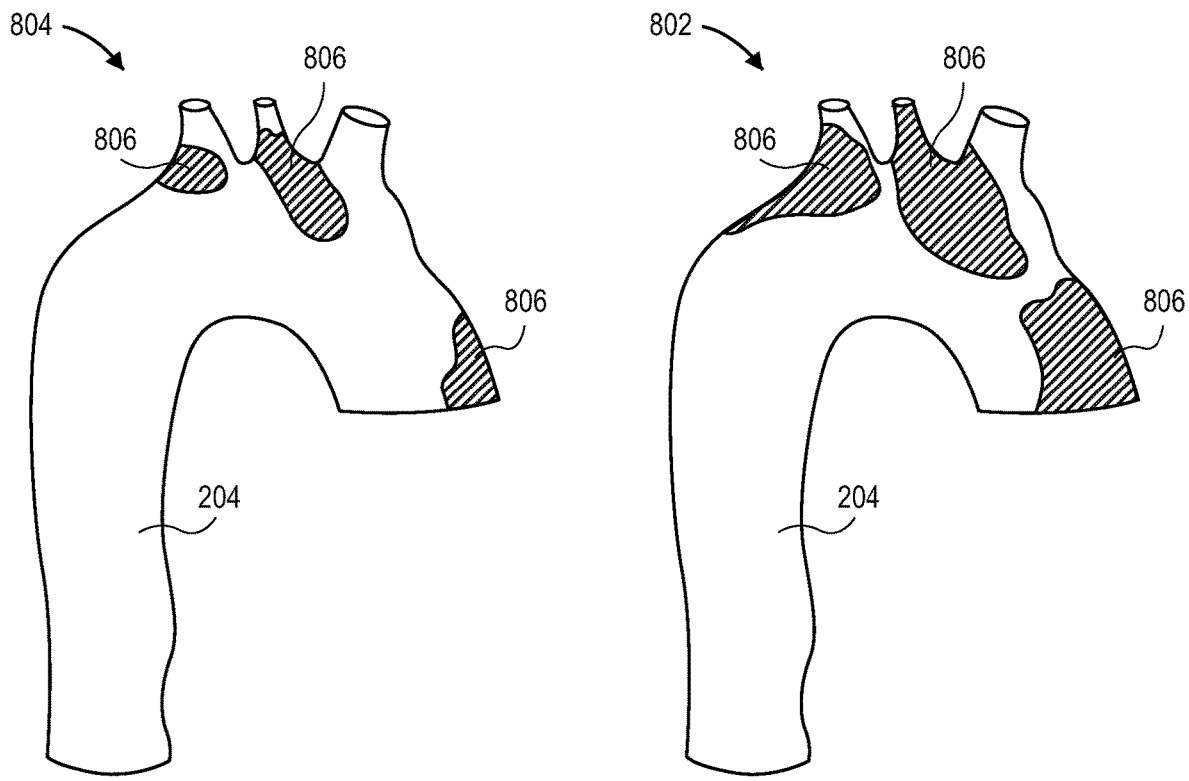
FIG. 8 is a pictorial view of a vessel segment modeled using different parameters of a personalized model of a vascular system, in accordance with an embodiment.

Referring to FIG. 8, a pictorial view of a vessel segment modeled using different parameters of a personalized model of a vascular system is shown in accordance with an embodiment. In an embodiment, the simulated flow estimates one or more of a flow velocity, a wall shear stress, or a wall pressure of the vessel segment 204. The vessel segment 204 illustrated at the right of the figure can be a control simulation 802. In the control simulation 802, the second vascular system model 602 that was personalized to the patient in FIG. 5 can be used to estimate a wall pressure of the vessel segment 204. Areas of pressure 806 within a certain range, e.g., a higher pressure range, are shown in cross-hatching. These high pressure areas may indicate, for example, regions of the vessel segment 204 that are more susceptible to aneurysm. The vessel segment 204 illustrated at the left of the figure can be a test simulation 804. In the test simulation 804, the second vascular system model 602 can be altered by physician inputs to predict the effect a therapeutic substance on the patient. For example, the 0D model parameters of the remainder of the vasculature can be changed to emulate the reduction in systemic blood pressure that is induced by the use of the therapeutic substance. In the test simulation 804, the cross-hatched regions that indicate higher pressure ranges may reduce in size. For example, the regions of high pressure around the ostia can become smaller. Such simulations can be performed in real-time, and can provide the physician with a valuable predictive tool to determine a risk of disease for the patient.

Figure 9:
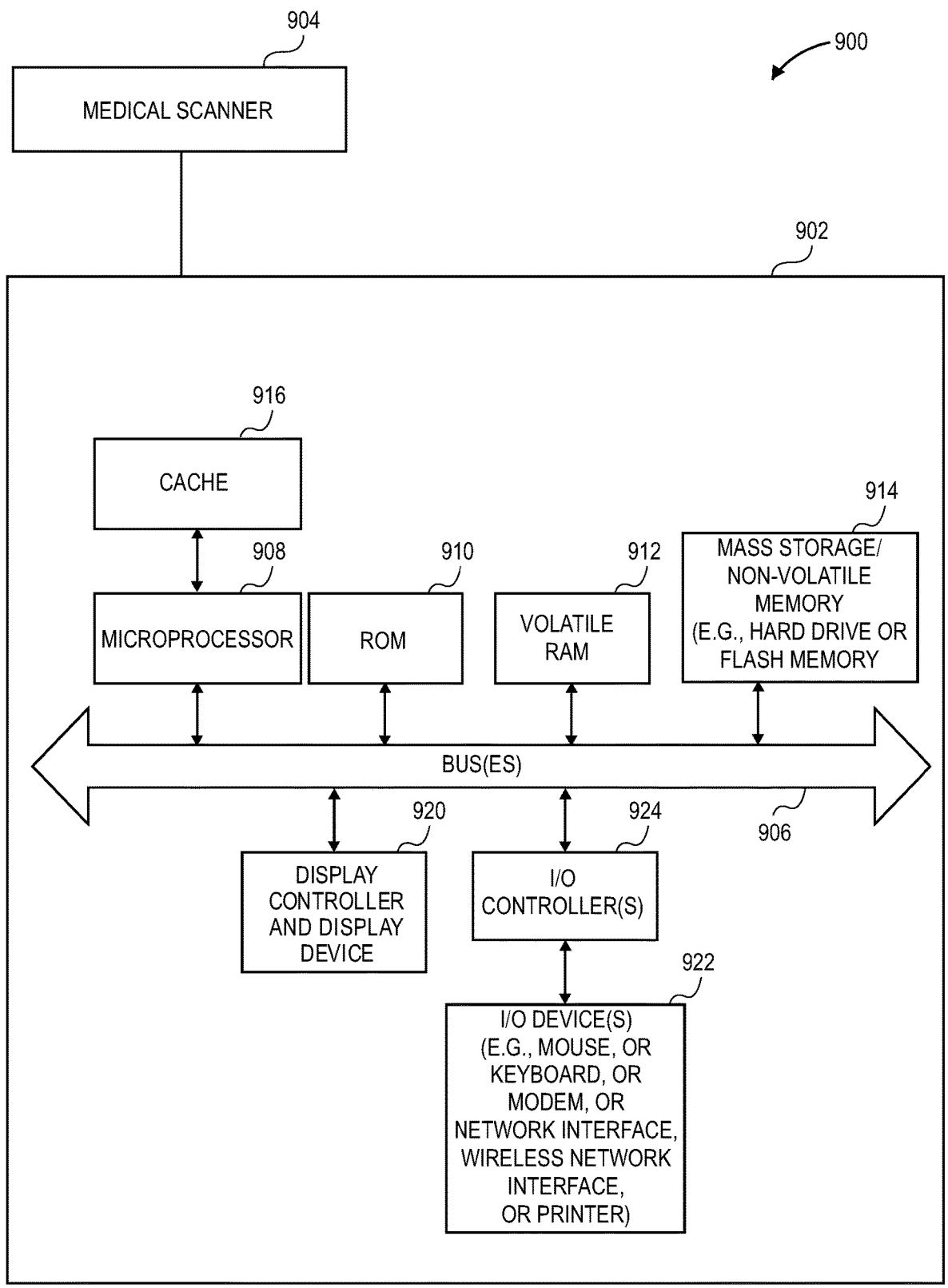
FIG. 9 is a schematic view of a system configured to perform a method of modeling a vasculature in near real-time, in accordance with an embodiment.

Referring to FIG. 9, a schematic view of a system configured to perform a method of modeling a vasculature in near real-time is shown in accordance with an embodiment. The methods described above can be embodied as embedded software in a medical imaging system, e.g., an MRI machine, or as software running on a data processing system 902 in a clinician's office, for example. The methods can be computer implemented methods performed by a data processing system 902 to provide accurate evaluations and outcome predictions for vascular disease treatments.

Note that while FIG. 9 illustrates various components of a data processing system 902, it is not intended to represent any particular architecture or manner of interconnecting the components as such details are not germane to this description. It will also be appreciated that network computers, tablet computers, consumer electronic devices and other data processing systems 902 which have fewer components or perhaps more components may also be used with one or more embodiments described herein.

As shown in FIG. 9, a system 900 can include a data processing system 902. The system 900 is optionally a medical imaging system including a medical scanner 904, e.g., a CT or MRI machine. In such case, the data processing system 902 can be included as part of the medical imaging system. Alternatively, the data processing system 902 may be a standalone computer system that is interconnected, e.g., directly coupled or networked with, the medical scanner 904. In any case, the medical scanner can 904 generate medical scan data and/or the 3D data 202 representing the vessel segment 204, and the data processing system 902 can receive the 3D data 202.

In an embodiment, the data processing system 902 includes a bus 906 which is couple to one or more processors 908 and a memory, e.g., ROM (Read Only Memory) 910 or volatile RAM (Random Access Memory) 912 or a non-volatile memory 914. The one or more processors 908 can be coupled to optional cache 916. The one or more processors 908 may retrieve the stored instructions from one or more of the memories 910, 912, or 914 and execute the instructions to perform the operations described above. These memories represent examples of non-transitory machine or computer-readable storage media that can store or contain computer program instructions which when executed cause the system 900 to perform the one or more methods described herein. For example, the memories can receive or store the 3D data 202 representing the vessel segment 204 from the medical scanner 904, and the one or more processors may access the 3D data 202 and the instructions to perform the operations that generate the reduced order model 504 of the vessel segment 204. Similarly, the memories can receive and store the measured flow data and/or the simulated flow data, and the one or more processors can access the data and the instructions to perform the comparison of the data and the optimization of the 0D model 402 of the remainder of the vasculature.

The bus 906 interconnects the processor(s), memor(ies), and optional cache together and also interconnects these components to a display controller and display device 920 and to peripheral devices such as input/output (I/O) devices 922 which may be one or more of mice, touch screens, touch pads, touch sensitive input devices, keyboards, modems, network interfaces, printers and other devices which are well known in the art. The display device 920 can output images, such as those illustrated in FIG. 8, and the input device can receive user inputs, such as the input to update parameters at operation 702. Typically, the input/output devices 922 are coupled to the system through input/output controllers 924. The volatile RAM 912 is typically implemented as dynamic RAM (DRAM) which requires power continually in order to refresh or maintain the data in memory.

The mass storage 914 is typically a magnetic hard drive or a magnetic optical drive or an optical drive or a DVD RAM or a flash memory or other types of memory system which maintain data (e.g., large amounts of data) even after power is removed from the system. Typically the mass storage 914 will also be a random access memory although this is not required. While FIG. 9 shows that the mass storage 914 is a local device coupled directly to the rest of the components in the data processing system 902, it will be appreciated that one or more embodiments may utilize a non-volatile memory which is remote from the system, such as a network storage device which is coupled to the data processing system 902 through a network interface such as a modem, an Ethernet interface or a wireless network. For example, the non-volatile memory may be contained within the medical imaging system having the medical scanner 904, which is networked to the data processing system 902. The bus 906 may include one or more buses connected to each other through various bridges, controllers and/or adapters as is well known in the art.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A non-transitory computer-readable medium storing instructions, which when executed by one or more processors of a system, causes the system to perform a method, comprising:
   receiving 3D data representing a vessel segment of a vasculature;
   determining a 0D model of the vessel segment based on static fluid simulations of the vessel segment using the 3D data, wherein the 0D model includes a respective inductor and a respective pressure source for each of a plurality of subsegments extending between an inlet and a plurality of outlets of the vessel segment, and wherein values of the pressure sources are taken from a response surface of the static fluid simulations of the vessel segment;
   generating a set of boundary conditions of the vessel segment based on a first vascular system model including the 0D model of the vessel segment coupled to a 0D model of a remainder of the vasculature; and
   generating a reduced order model of the vessel segment based on transient fluid simulations of the vessel segment using the set of boundary conditions, wherein the reduced order model represents flow in the vessel segment in real-time.

2. The non-transitory computer-readable medium of claim 1, wherein the set of boundary conditions includes a pressure profile or a flow profile of the vessel segment.

3. The non-transitory computer-readable medium of claim 1, wherein the reduced order model of the vessel segment computes pressure at the plurality of outlets.

4. The non-transitory computer-readable medium of claim 1 further comprising:

receiving measured flow data representing measurements of flow in the vessel segment;

generating simulated flow data representing flow in the vessel segment based on a second vascular system model including the reduced order model of the vessel segment coupled to the 0D model of the remainder of the vasculature; and adjusting the 0D model of the remainder of the vasculature based on a comparison of the simulated flow data to the measured flow data.

5. The non-transitory computer-readable medium of claim 4 further comprising:

receiving an input to update parameters of the 0D model of the remainder of the vasculature; and simulating flow in the vessel segment in near real-time using the second vascular system model including the reduced order model of the vessel segment coupled to the 0D model of the remainder of the vasculature having the updated parameters.

6. The non-transitory computer-readable medium of claim 5, wherein the updated parameters include a resistance, a capacitance, or an inductance of the 0D model of the remainder of the vasculature.

7. The non-transitory computer-readable medium of claim 5, wherein the simulated flow estimates one or more hemodynamic characteristics of the remainder of the vasculature based on the updated parameters.

8. The non-transitory computer-readable medium of claim 5, wherein the simulated flow estimates a flow velocity, a wall shear stress, or a wall pressure of the vessel segment.

9. A system, comprising:

a memory to receive 3D data representing a vessel segment of a vasculature; and one or more processors to determine a 0D model of the vessel segment based on static fluid simulations of the vessel segment using the 3D data, wherein the 0D model includes a respective inductor and a respective pressure source for each of a plurality of subsegments extending between an inlet and a plurality of outlets of the vessel segment, and wherein values of the pressure sources are taken from a response surface of the static fluid simulations of the vessel segment, generate a set of boundary conditions of the vessel segment based on a first vascular system model including the 0D model of the vessel segment coupled to a 0D model of a remainder of the vasculature, and generate a reduced order model of the vessel segment based on transient fluid simulations of the vessel segment using the set of boundary conditions, wherein the reduced order model represents flow in the vessel segment in real-time.

10. The system of claim 9, wherein the memory is further to receive measured flow data representing measurements of flow in the vessel segment, and wherein the one or more processors are further to generate simulated flow data representing flow in the vessel segment based on a second vascular system model including the reduced order model of the vessel segment coupled to the 0D model of the remainder of the vasculature, and adjust the 0D model of the remainder of the vasculature based on a comparison of the simulated flow data to the measured flow data.

11. The system of claim 10 further comprising an input device to receive an input to update parameters of the 0D model of the remainder of the vasculature, wherein the one or more processors are further to simulate flow in the vessel segment in near real-time using the second vascular system model including the reduced order model of the vessel segment coupled to the 0D model of the remainder of the vasculature having the updated parameters.

12. The system of claim 9 further comprising a medical scanner to generate the 3D data representing the vessel segment.

13. A non-transitory computer-readable medium storing instructions, which when executed by one or more processors of a system, cause the system to perform a method, comprising:

receiving 3D data representing a vessel segment of a vasculature;

determining a 0D model of the vessel segment based on static fluid simulations of the vessel segment using the 3D data, wherein the 0D model includes a respective inductor and a respective pressure source for each of a plurality of subsegments extending between an inlet and a plurality of outlets of the vessel segment, and wherein values of the pressure sources are taken from a response surface of the static fluid simulations of the vessel segment;

receiving measured flow data representing measurements of flow in the vessel segment;

generating simulated flow data representing flow in the vessel segment based on a first vascular system model including a reduced order model of the vessel segment coupled to a 0D model of a remainder of the vasculature, wherein the reduced order model represents flow in the vessel segment in real-time, and wherein the reduced order model is based on the 0D model of the vessel segment; and adjusting the 0D model of the remainder of the vasculature based on a comparison of the simulated flow data to the measured flow data.

14. The non-transitory computer-readable medium of claim 13 further comprising:

generating a set of boundary conditions of the vessel segment based on a second vascular system model including the 0D model of the vessel segment coupled to the 0D model of the remainder of the vasculature; and generating the reduced order model of the vessel segment based on transient fluid simulations of the vessel segment using the set of boundary conditions.

15. The non-transitory computer-readable medium of claim 14, wherein the set of boundary conditions includes a pressure profile or a flow profile of the vessel segment.

16. The non-transitory computer-readable medium of claim 13, wherein the reduced order model of the vessel segment computes pressure at the plurality of outlets.

17. The non-transitory computer-readable medium of claim 13 further comprising:

receiving an input to update parameters of the 0D model of the remainder of the vasculature; and simulating flow in the vessel segment in real-time using the first vascular system model including the reduced order model of the vessel segment coupled to the 0D model of the remainder of the vasculature having the updated parameters.

18. The non-transitory computer-readable medium of claim 17, wherein the updated parameters include a resistance, a capacitance, or an inductance of the 0D model of the remainder of the vasculature.

19. The non-transitory computer-readable medium of claim 17, wherein the simulated flow estimates one or more hemodynamic characteristics of the remainder of the vasculature based on the updated parameters.

20. The non-transitory computer-readable medium of claim 17, wherein the simulated flow estimates a flow velocity, a wall shear stress, or a wall pressure of the vessel segment.

21. A system, comprising:
a memory to receive 3D data representing a vessel segment of a vasculature and measured flow data representing measurements of flow in the vessel segment; and
one or more processors to
determine a 0D model of the vessel segment based on static fluid simulations of the vessel segment using the 3D data, wherein the 0D model includes a respective inductor and a respective pressure source for each of a plurality of subsegments extending between an inlet and a plurality of outlets of the vessel segment, and wherein values of the pressure sources are taken from a response surface of the static fluid simulations of the vessel segment,
generate simulated flow data representing flow in the vessel segment based on a first vascular system model including a reduced order model of the vessel segment coupled to a 0D model of a remainder of the vasculature, wherein the reduced order model represents flow in the vessel segment in real-time, and wherein the reduced order model is based on the 0D model of the vessel segment, and
adjust the 0D model of the remainder of the vasculature based on a comparison of the simulated flow data to the measured flow data.

22. The system of claim 21, wherein the memory is further to receive 3D data representing the vessel segment, and wherein the one or more processors are further to
generate a set of boundary conditions of the vessel segment based on a second vascular system model including the 0D model of the vessel segment coupled to the 0D model of the remainder of the vasculature, and
generate the reduced order model of the vessel segment based on transient fluid simulations of the vessel segment using the set of boundary conditions.

23. The system of claim 21 further comprising an input device to receive an input to update parameters of the 0D model of the remainder of the vasculature, and wherein the one or more processors are further to simulate flow in the vessel segment in near real-time using the first vascular system model including the reduced order model of the vessel segment coupled to the 0D model of the remainder of the vasculature having the updated parameters.

24. The system of claim 21 further comprising a medical scanner to generate the measured flow data.

* * * * *